(12) United States Patent
Cage et al.

(10) Patent No.: US 9,358,070 B2
(45) Date of Patent: Jun. 7, 2016

(54) MEDICAL DEVICE PACKAGE AND METHODS

(71) Applicants: Logan Michael Cage, Bloomington, IN (US); Elizabeth Anne Theobald, Bloomington, IN (US); Kurt J. Tekulve, Ellettsville, IN (US); Steve Harris, Vernon Hills, IL (US); Ryan Koontz, Bedford, IN (US)

(72) Inventors: Logan Michael Cage, Bloomington, IN (US); Elizabeth Anne Theobald, Bloomington, IN (US); Kurt J. Tekulve, Ellettsville, IN (US); Steve Harris, Vernon Hills, IL (US); Ryan Koontz, Bedford, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 528 days.

(21) Appl. No.: 13/746,018

(22) Filed: Jan. 21, 2013

(65) Prior Publication Data

US 2013/0197618 A1 Aug. 1, 2013

Related U.S. Application Data

(60) Provisional application No. 61/590,862, filed on Jan. 26, 2012.

(51) Int. Cl.
| | |
|---|---|
| *A61B 17/22* | (2006.01) |
| *B65D 83/10* | (2006.01) |
| *A61B 19/02* | (2006.01) |
| *B65B 5/04* | (2006.01) |
| *A61F 2/95* | (2013.01) |
| *A61F 2/00* | (2006.01) |
| *A61B 17/12* | (2006.01) |
| *A61B 17/00* | (2006.01) |

(52) U.S. Cl.
CPC ........... *A61B 19/026* (2013.01); *A61B 17/1214* (2013.01); *A61B 17/12109* (2013.01); *A61F 2/0095* (2013.01); *A61F 2/95* (2013.01); *B65B 5/04* (2013.01); *A61B 17/1215* (2013.01); *A61B 2017/00526* (2013.01); *B65B 2220/16* (2013.01)

(58) Field of Classification Search
None
See application file for complete search history.

(56) References Cited

U.S. PATENT DOCUMENTS

| | | | |
|---|---|---|---|
| 4,181,223 A | 1/1980 | Millet | |
| 4,994,069 A * | 2/1991 | Ritchart et al. | 606/191 |
| 5,765,682 A * | 6/1998 | Bley et al. | 206/363 |
| 7,328,794 B2 | 2/2008 | Lubs et al. | |
| 7,694,810 B1 | 4/2010 | Barry et al. | |
| 2009/0120819 A1 | 5/2009 | Delli-Santi et al. | |
| 2010/0152650 A1 | 6/2010 | Schrodt | |
| 2010/0160953 A1 | 6/2010 | Ngo et al. | |
| 2010/0290723 A1 | 11/2010 | Shinozaki et al. | |

* cited by examiner

*Primary Examiner* — Tuan V Nguyen
(74) *Attorney, Agent, or Firm* — Liell & McNeil

(57) ABSTRACT

A medical device package includes an elongate tubular holder having a first and a second detachable tip, and a medical device positioned within a cavity and contained within the holder via the first and second detachable tips. The medical device has a self-shaping bias and is loaded in opposition to the bias via contact with an inner surface of the holder defining the cavity. The first and second detachable tips may include snap-off tips, such that upon detachment the cavity is opened for removing the medical device. Related methodology is disclosed.

20 Claims, 4 Drawing Sheets

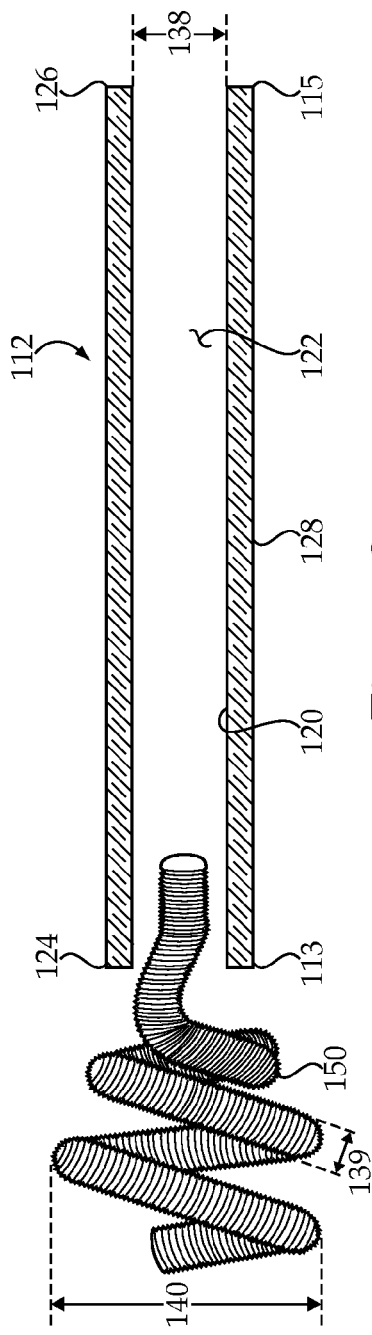
Figure 2
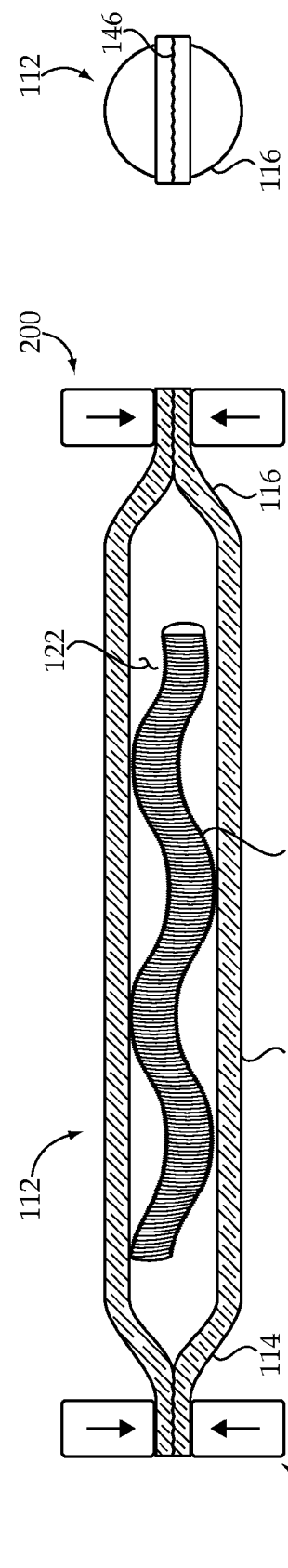
Figure 7
Figure 3

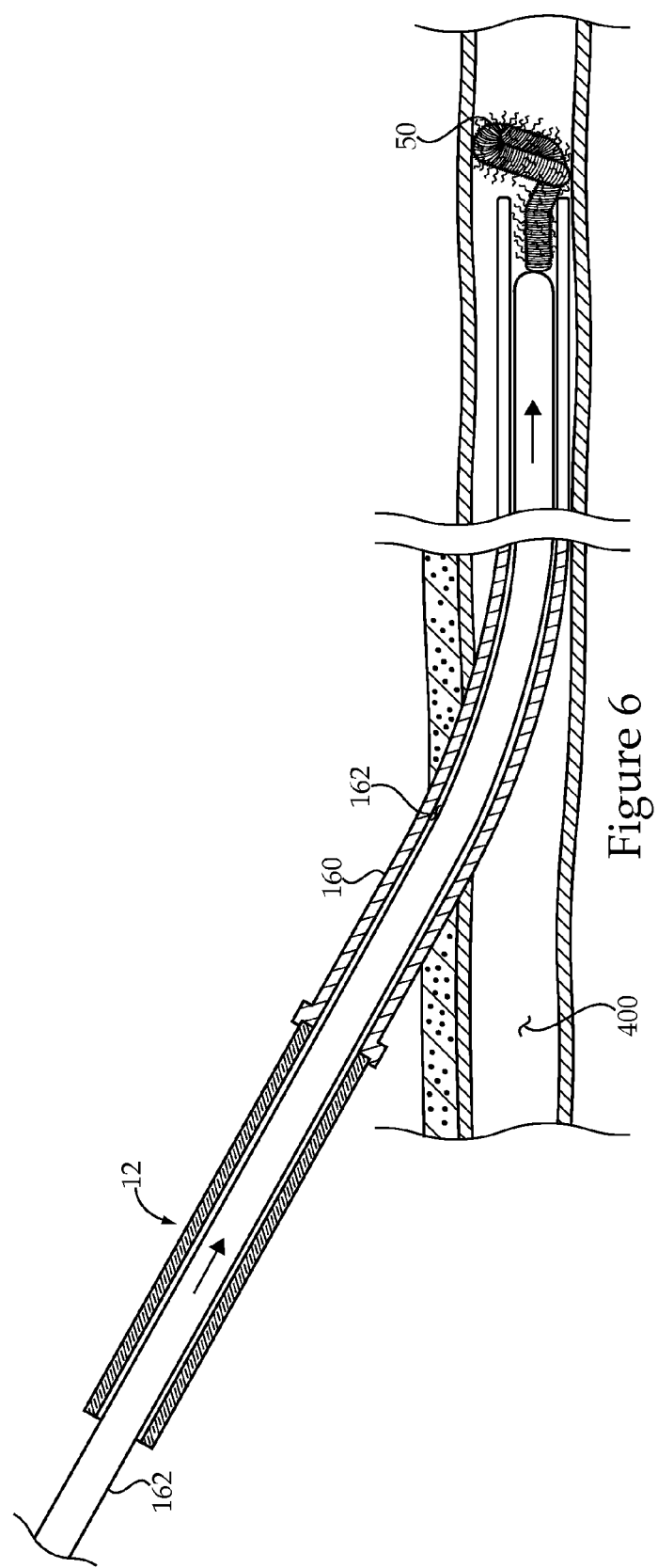

MEDICAL DEVICE PACKAGE AND METHODS

RELATION TO OTHER PATENT APPLICATION

This application claims priority to provisional patent application 61/590,862, filed Jan. 26, 2012 with the same title.

TECHNICAL FIELD

The present disclosure relates generally to medical device packaging, and relates more particularly to containing a medical device within an elongate tubular holder via detachable tips.

BACKGROUND

Medical devices are packaged in many different ways. Devices to be used intraluminally within a patient are, of course, subject to sterilization requirements, affecting selection of materials for packaging, and in some instances the construction or design of the package itself. Still other concerns related to the relative ease of removing medical devices from a package, and suitability of packaging materials for long term storage. For these and other reasons, a great diversity of packaging materials and packaging design has developed over the years.

One class of medical device commonly packaged in a specialized manner includes those made from shape memory materials. Such devices may need to be loaded into a delivery catheter or the like in a state different from the natural rest state of the device. Packaging tubes and the like are commonly used to maintain the device in a state suitable for loading. U.S. Pat. No. 5,765,682 to Bley et al. is directed to a package for a medical device made of an expandable or shape memory material. The package includes a sheath containing the medical device, and having a tear away or peel away feature which provides easy access to the medical device when needed. While Bley et al. may work well for its intended purposes, the techniques are less well suited to certain types of medical devices and device delivery strategies.

SUMMARY OF DISCLOSURE

In one aspect, a medical device package includes an elongate tubular holder having a first and a second detachable tip, and an inner surface defining a cavity extending longitudinally between the first and second detachable tips. The package further includes a medical device positioned within the cavity, the medical device having a self-shaping bias and being loaded in opposition to the self-shaping bias via contact with the inner surface. The first and second detachable tips contain the medical device within the cavity, such that detaching the first and second detachable tips opens the cavity for removing the medical device from the elongate tubular holder.

In another aspect, a method of packaging a medical device includes positioning a medical device having a self-shaping bias within a cavity in an elongate tubular holder, and applying a load to the medical device opposing the self-shaping bias, during the step of positioning. The method further includes containing the loaded medical device within the cavity via first and second detachable tips of the elongate tubular holder.

In still another aspect, a method of percutaneously treating a patient includes detaching a first and a second tip of an elongate tubular holder containing a medical device, and pushing the medical device from the elongate tubular holder into an introducer. The introducer extends into a body lumen of the patient through an opening in the patient's skin. The method further includes advancing the medical device from the introducer into the body lumen such that the medical device self-deploys therein.

BRIEF DESCRIPTION OF THE DRAWINGS

FIG. 2 is a partially sectioned side diagrammatic view at one stage of a medical device packaging procedure, according to one embodiment;

FIG. 3 is a partially sectioned side diagrammatic view at another stage of the packaging procedure;

FIG. 6 is a partially sectioned diagrammatic view at another stage of the treatment procedure; and FIG. 7 is an end view of a medical device package, according to one embodiment.

DETAILED DESCRIPTION

Figure 1:
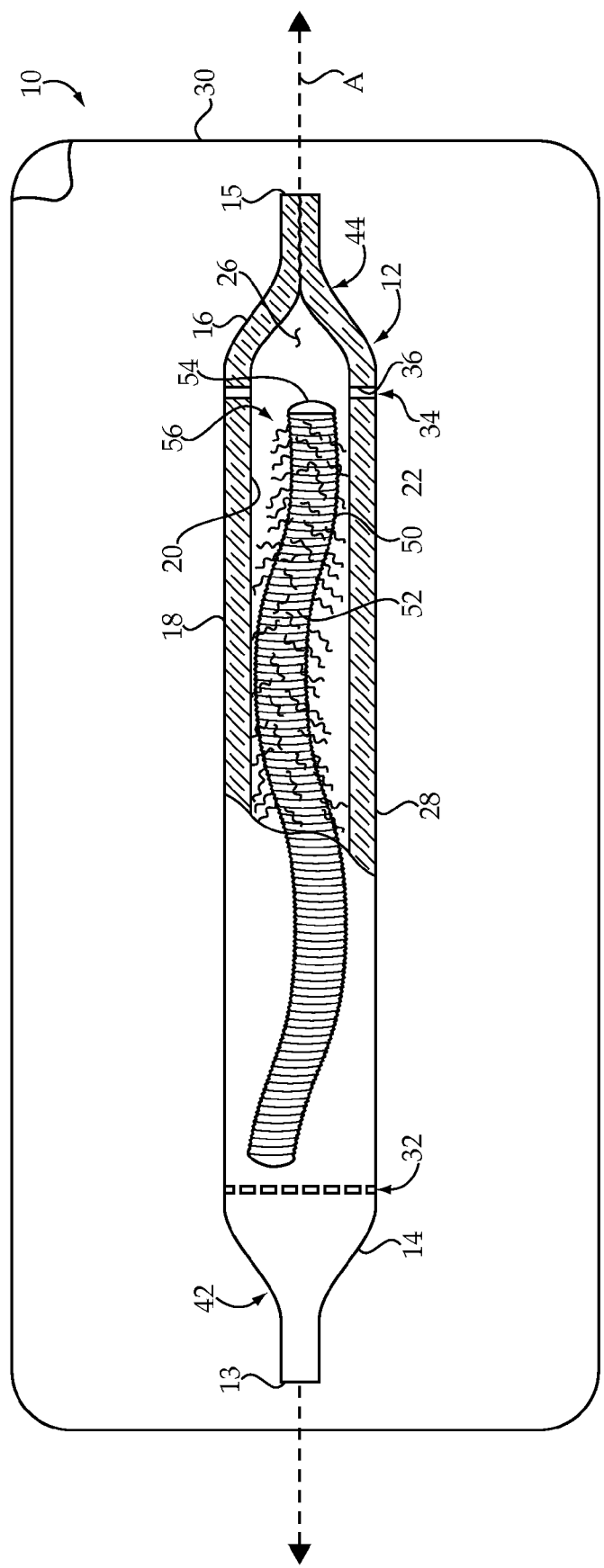
FIG. 1 is a partially sectioned side diagrammatic view of a medical device package, according to one embodiment.

Referring to FIG. 1, there is shown a medical device package 10 according to one embodiment. Package 10 includes an elongate tubular holder 12 having a first end 13 including a first detachable tip 14, and a second end 15 having a second detachable tip 16. Holder 12 further includes an outer surface 18, and an inner surface 20 defining a cavity 22 extending longitudinally between first and second detachable tips 14 and 16. A medical device 50 is positioned within cavity 22. Device 50 includes a self-shaping bias and is loaded in opposition to the self-shaping bias via contact with inner surface 20. First and second detachable tips 14 and 16 contain device 50 within cavity 22, such that detaching tips 14 and 16 opens cavity 22 for removing device 50 from holder 12. In the illustrated embodiment, package 10 is gas permeable, and is contained within a gas permeable envelope 30 such as a sterile, peel-open envelope, the significance of which will be apparent from the following description.

In a practical implementation strategy, holder 12 may be one-piece, and includes a tube body 28 having a cylindrical shape, with first and second tips 14 and 16 being formed integrally with tube body 28. Holder 12 may further define a longitudinal axis A, and has a first weakened break zone 32 and a second weakened break zone 34. First detachable tip 14 may be located axially outward of first break zone 32, whereas second detachable tip 16 may be located axially outward of second break zone 34. In the illustrated embodiment, one end 26 of cavity 22 resides in second detachable tip 16, whereas an opposite end of cavity 22, which is not visible in FIG. 1, resides in first tip 14. Each of tips 14 and 16 may be formed by crimping, as further discussed herein, and thus first tip 14 includes a first taper 42 and second tip 16 includes a second taper 44, as may result from deforming opposite ends of a tube used as a starting component for making holder 12. Tips 14 and 16, as well as break zones 32 and 34, may be formed subsequent to positioning device 50 within cavity 22, as further discussed herein. In a practical implementation strategy, break zones 32 and 34 may be formed axially outward of device 50, such that upon detaching tips 14 and 16, no part of device 50 extends out of holder 12.

Device 50 may include an embolization device, and in certain embodiments may include a wire embolization coil. To this end, device 50 may include a helically coiled wire 52 having a tip 54, and a plurality of fibers 56 attached to wire 52 in a conventional manner. Device 50 may be held in a lengthened state within cavity 22 via the loading opposing its self-shaping bias, and may be adjustable to a curled rest state via the self-shaping bias as further described herein.

Referring now to FIG. 2, there is shown another holder 112 as it might appear prior to forming detachable tips and weakened break zones, and while positioning a medical device 150 therein. Medical device 150 has certain similarities with device 50 of FIG. 1, and may also include a wire embolization coil. For illustrative purposes, medical device 150 is depicted as an embodiment free of fibers, and is relatively longer than medical device 50 but may otherwise have analogous self-shaping properties. Holder 112 includes an elongate cylindrical tube body 128 having an inner surface 120 defining a cavity 122. Device 150 is shown as it might appear during sliding into an open end 124 of cavity 122 towards an opposite open end 126. During sliding device 150 into open end 124, device 150 is uncurled in opposition to its self-shaping bias. Inner surface 120 may define an inner diameter 138, and device 150 may define a coil diameter 139 and a curl diameter 140. Curl diameter 140 is larger than inner diameter 138, and coil diameter 139 is smaller than inner diameter 138. It will thus be appreciated that device 150 includes a curled rest state, and is adjusted to a lengthened state via applying a load opposing its self-shaping bias during positioning device 150 within cavity 122. The curled rest state of device 150 includes a generally helical shape, however, the present disclosure is not thereby limited and a great many different medical devices having a broad array of rest state shapes may be used in the context of the present disclosure. The present disclosure is also applicable to packaging medical devices having a range of sizes. To this end, devices such as embolization devices packaged according to the present techniques may have lengths ranging from 0.5 cm to 30 cm. In other words, a medical device such as devices 50 or 150 may have a length when elastically deformed to a substantially linear shape (without spreading out the coil of the wire) which is within this range. Coil diameters of embolization devices contemplated herein may be from 0.02 cm to 0.13 cm. Curl diameter dimensions may be 5 cm or less.

Referring to FIG. 3, there is shown holder 112 with device 150 positioned therein, and as it might appear during forming tips 114 and 116. In one practical implementation strategy, tips 114 and 116 may be formed by crimping the opposite ends of tube body 128. To this end, crimping tools 200 are shown having just been actuated to deform material of tube body 128. Tube body 128 may be formed from any suitable material, examples of which are glass materials, poly methyl methacrylate material such as Plexiglas®, and various polymeric materials. The material of tube body 128 may be transparent or translucent in certain embodiments, and may be heated prior to or during crimping tube body 128 to assist in plastically deforming tube body 128. FIG. 7 illustrates an end view of holder 112 after forming tips 114 and 116, showing an abutment 146 between layers of the material of body 128.

Figure 4:
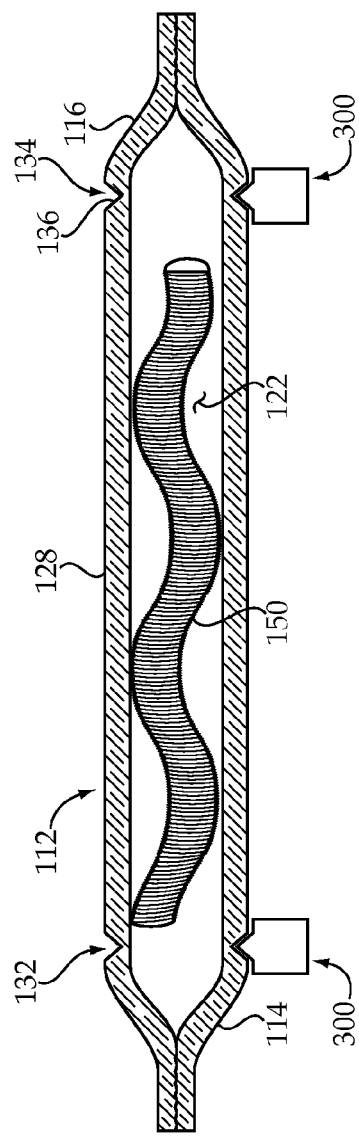
FIG. 4 is a partially sectioned side diagrammatic view at yet another stage of the packaging procedure.

Referring now to FIG. 4, there is shown holder 112 with device 150 positioned therein, as it might appear after forming tips 114 and 116 and during forming break zones 132 and 134. Break zones 132 and 134 might include a scoring or perforation(s). To this end, a scoring tool 300 is shown engaged with tube body 128 to form score lines 136 at positions outward of device 150. As noted above, holder 112 may be gas permeable. Gas permeability of holder 112 enables gas sterilization of holder 112 and other holder embodiments contemplated herein in a known manner. Gas permeability of holder 112 may be achieved by crimping or otherwise modifying tube body 128 such that tips 114 and 116 do not fluidly seal cavity 122, but only physically block the ends of cavity 122 to contain device 150 therein. Gas permeability might also be achieved via perforations as in the embodiment of FIG. 1. Whether scoring, perforations, or another strategy is used to form break zones 132 and 134, the respective break zones may be circumferential of holder 112 such that they extend all the way around tube body 128. In this general manner, break zones 132 and 134 provide a controlled location for snapping off tips 114 and 116. By defining a location of detachment of tips 114 and 116, they may be removed in a manner which ensures that device 150 will not be exposed and protrude from tube body 128, risking contact with non-sterile surfaces and the like, and also ensuring that sufficient material will be snapped off to allow removal of device 150. In other words, without a controlled location for snapping off tips 114 and 116, there might be some risk that tips 114 and 116 might be snapped off inwardly of a desired location, exposing device 150, or outwardly of the desired location, and not removing a sufficient extent of the tip to allow device 150 to be removed. Still another way to understand these principles is that the inner diameter of holder 112 is not compromised, preventing removal of device 150, nor is a protective length of holder 112 compromised, exposing device 150 outside holder 112. This general snap-off strategy, as well as the example materials set forth herein, also ensures that particulates or other debris from holder 112 are not created which could find their way into or onto device 150 and eventually end up within a patient during treatment. Descriptions herein of one of holders 12 or 112 should be understood to refer analogously to the other of holders 12 or 112, except where otherwise indicated.

INDUSTRIAL APPLICABILITY

Figure 5:
FIG. 5 is a partially sectioned side diagrammatic view at one stage of a treatment procedure, according to one embodiment.

Referring now to FIG. 5, there is shown holder 12 as it might appear having been removed from envelope 30 and coupled with an introducer 160 or the like extending into a body lumen 400 of a patient such as a vein or artery. Introducer 160 includes a lumen 162 which has been aligned with and placed in communication with cavity 22 in holder 12. Tips 14 and 16 have been snapped off, and a pusher 162 such as a wire has been passed into holder 12 to commence pushing device 50 into lumen 162. Referring also to FIG. 6, there is shown a subsequent procedural stage, in which pusher 162 has been further slid through holder 12 and introducer 160, to push device 50 through lumen 162, and advance device 50 from introducer 160 into body lumen 400 such that device 50 self-deploys therein. In the illustrated embodiment, device 50 has been advanced into body lumen 400 such that device 50 assumes a curled state within body lumen 400 via its self-shaping bias. From the stage depicted at FIG. 6, device 50 may form an embolism within the patient in a conventional manner, and might be left within the patient or removed by way known techniques.

As noted above, embolization devices are often stored in tubes to facilitate loading into catheter devices for deployment. A bent wire mandrel that prevents the embolization device from falling out of the tube is typically removed, and the tube loaded into an end of a catheter, introducer sheath, or analogous device outside of a patient. Such bent wire mandrels can slip out of the tube during transport, or during transfer in the operating room. Since the tubes typically hold the embolization device in a lengthened state for loading, where bent wire mandrels slip out of the tube, there is a risk that the embolization device itself will fall out of the tube, and be difficult to reload. Worse, the embolization device can fall onto the floor and be rendered non-sterile, and thus must be discarded. The present disclosure ensures that medical devices, such as embolization coils and the like, cannot fall out of a package until completely ready to load into a catheter or similar introducer during a procedure. Moreover, forming the tips of the holder to be detachable, and advantageously snap-off, provides a quick and efficient, as well as reliable strategy for addressing the foregoing and other concerns.

The present description is for illustrative purposes only, and should not be construed to narrow the breadth of the present disclosure in any way. Thus, those skilled in the art will appreciate that various modifications might be made to the presently disclosed embodiments without departing from the full and fair scope and spirit of the present disclosure. Other aspects, features and advantages will be apparent upon an examination of the attached drawings and appended claims.

What is claimed is:

1. A medical device package comprising:
an elongate tubular holder including a first and a second detachable tip, wherein the elongate tubular holder, the first detachable tip and the second detachable tip are a gas-permeable one-piece member, and an inner surface defining a cavity extending longitudinally between the first and second detachable tips;
a medical device positioned within the cavity, the medical device having a self-shaping bias and being loaded in opposition to the self-shaping bias via contact with the inner surface; and
the first and second detachable tips containing the medical device within the cavity, such that detaching the first and second detachable tips opens the cavity for removing the medical device from the elongate tubular holder.

2. The package of claim 1 wherein the medical device includes an embolization device.

3. The package of claim 2 wherein the medical device includes a wire embolization coil.

4. The package of claim 3 wherein the medical device is held in a lengthened state within the cavity via the loading, and is adjustable to a curled rest state via the self-shaping bias when the medical device is removed from the elongated tubular holder.

5. The package of claim 4 wherein the elongate tubular holder defines an inner diameter, and the medical device defines a curl diameter in the curled rest state which is larger than the inner diameter.

6. The package of claim 2 wherein the elongate tubular holder defines a longitudinal axis, and further includes a first and a second weakened break zone, and wherein the first and second detachable tips each include a snap-off tip located axially outward of the first and second weakened break zones, respectively.

7. The package of claim 6 wherein the elongate tubular holder further includes a uniform inner diameter extending from the first weakened break zone to the second weakened break zone.

8. The package of claim 7 wherein each of the weakened break zones includes a scoring or a perforation.

9. The package of claim 8 wherein each of the weakened break zones is circumferential of the elongate tubular holder.

10. The package of claim 6 wherein the first and second detachable tips each include a taper, and the tapers narrow in opposite axially outward directions.

11. A medical device package comprising:
an elongate tubular holder including a first and a second detachable tip, and an inner surface defining a cavity extending longitudinally between the first and second detachable tips;
a medical device positioned within the cavity, the medical device having a self-shaping bias and being loaded in opposition to the self-shaping bias via contact with the inner surface;
the first and second detachable tips containing the medical device within the cavity, such that detaching the first and second detachable tips opens the cavity for removing the medical device from the elongate tubular holder;
wherein the medical device includes an embolization device; and
wherein the elongate tubular holder is gas permeable, and further comprising a gas impermeable envelope containing the elongate tubular holder.

12. A method of packaging a medical device that includes an elongate tubular holder including a first and a second detachable tip, wherein the elongate tubular holder, the first detachable tip and the second detachable tip are a gas-permeable one-piece member, and an inner surface defining a cavity extending longitudinally between the first and second detachable tips; a medical device positioned within the cavity, the medical device having a self-shaping bias and being loaded in opposition to the self-shaping bias via contact with the inner surface; and the first and second detachable tips containing the medical device within the cavity, such that detaching the first and second detachable tips opens the cavity for removing the medical device from the elongate tubular holder, and the method comprising the steps of:
positioning the medical device having the self-shaping bias within the cavity in the elongate tubular holder;
applying a load to the medical device opposing the self-shaping bias, during the step of positioning;
crimping opposite ends of the elongate tubular holder to form the first and second detachable tips, respectively; and
containing the loaded medical device within the cavity via the first and second detachable tips of the elongate tubular holder.

13. The method of claim 12 wherein the step of positioning includes sliding the medical device into an open end of the cavity, and wherein the step of applying further includes uncurling the medical device during sliding into the open end of the cavity.

14. The method of claim 13 wherein the medical device includes an embolization coil defining a curl diameter greater than an inner diameter of the elongate tubular holder when the medical device is removed from the elongate tubular holder.

15. The method of claim 14 wherein each of the detachable tips includes a snap-off tip, and the step of containing further includes a step of forming the snap-off tips subsequent to the positioning and applying steps.

16. The method of claim 15 wherein the step of forming the snap-off tips further includes crimping opposite ends of the elongate tubular holder, and forming circumferential break zones in the elongate tubular holder at locations inward of the crimped opposite ends.

17. A method of packaging a medical device that includes an elongate tubular holder including a first and a second detachable tip, and an inner surface defining a cavity extending longitudinally between the first and second detachable tips; a medical device positioned within the cavity, the medical device having a self-shaping bias and being loaded in opposition to the self-shaping bias via contact with the inner surface; and the first and second detachable tips containing the medical device within the cavity, such that detaching the first and second detachable tips opens the cavity for removing the medical device from the elongate tubular holder, and the method comprising the steps of:

positioning the medical device having the self-shaping bias within the cavity in the elongate tubular holder;

applying a load to the medical device opposing the self-shaping bias, during the step of positioning;

containing the loaded medical device within the cavity via the first and second detachable tips of the elongate tubular holder;

forming the detachable tips, prior to the positioning and applying steps, to be snap-off tips by crimping opposite ends of the elongate tubular holder, and forming circumferential break zones in the elongate tubular holder at locations inward of the crimped opposite ends; and wherein the elongate tubular holder is gas permeable, and further comprising a step of placing the elongate tubular holder containing the medical device within a gas impermeable envelope.

18. A method of percutaneously treating a patient with medical device stored in an elongate tubular holder including a first and a second detachable tip, wherein the elongate tubular holder, the first detachable tip and the second detachable tip are a gas-permeable one-piece member, and an inner surface defining a cavity extending longitudinally between the first and second detachable tips; the medical device being positioned within the cavity, the medical device having a self-shaping bias and being loaded in opposition to the self-shaping bias via contact with the inner surface; and the first and second detachable tips containing the medical device within the cavity, such that detaching the first and second detachable tips opens the cavity for removing the medical device from the elongate tubular holder, the method comprising the steps of:

detaching the first and the second tip of the elongate tubular holder containing the medical device;

pushing the medical device from the elongate tubular holder into an introducer, the introducer extending into a body lumen of the patient through an opening in the patient's skin; and advancing the medical device from the introducer into the body lumen such that the medical device self-deploys therein.

19. The method of claim 18 wherein the step of detaching includes snapping off the detachable tips at weakened break zones extending circumferentially about the elongate tubular holder.

20. The method of claim 19 wherein the medical device includes a wire embolization coil held in a lengthened state opposed by a self-shaping bias thereof within the elongate tubular holder, and wherein the step of advancing includes advancing the embolization coil into the body lumen such that the embolization coil assumes a curled state within the body lumen via the self-shaping bias.

* * * * *